US012642984B1

(12) United States Patent  
Dijkstra et al.

(10) Patent No.: US 12,642,984 B1  
(45) Date of Patent: Jun. 2, 2026

(54) THERAPEUTIC PAD

(71) Applicant: Shenzhen Kaiyan Medical Equipment Co. Ltd, Shenzhen (CN)

(72) Inventors: Alain Dijkstra, Amstelveen (NL); Wen Caiyun, Shenzhen (CN); Zhou Hong, Shenzhen (CN); Zhou Jian, Shenzhen (CN)

(73) Assignee: Shenzhen Kaiyan Medical Equipment Co. Ltd (CN)

( * ) Notice: Subject to any disclaimer, the term of this patent is extended or adjusted under 35 U.S.C. 154(b) by 0 days.

(21) Appl. No.: 19/250,691

(22) Filed: Jun. 26, 2025

(51) Int. Cl.  
*A61N 5/06* (2006.01)

(52) U.S. Cl.  
CPC .... *A61N 5/0613* (2013.01); *A61N 2005/0652* (2013.01)

(58) Field of Classification Search  
CPC ................ A61N 5/0613; A61N 5/0616; A61N 2005/0632; A61N 2005/0635; A61N 2005/0636; A61N 2005/0638; A61N 2005/065; A61N 2005/0652  
USPC .......................................................... 607/91  
See application file for complete search history.

(56) References Cited

U.S. PATENT DOCUMENTS

| | | | | |
|---|---|---|---|---|
| 6,290,713 | B1 * | 9/2001 | Russell ................ | A61N 5/0616 607/91 |
| 7,070,611 | B2 * | 7/2006 | Biel ..................... | A61N 5/0601 128/872 |
| 2004/0044384 | A1 * | 3/2004 | Leber ................... | A61N 5/0619 607/96 |
| 2006/0217787 | A1 * | 9/2006 | Olson .................. | A61N 5/0616 607/88 |
| 2007/0100400 | A1 * | 5/2007 | Chung ................. | A61N 5/0621 607/88 |
| 2012/0289885 | A1 * | 11/2012 | Cottrell ................ | A61N 5/0616 604/20 |
| 2016/0045759 | A1 * | 2/2016 | Tapper ................. | A61N 5/0616 607/90 |
| 2020/0139152 | A1 * | 5/2020 | Behler ................. | A61N 5/0621 |
| 2025/0152968 | A1 * | 5/2025 | Dijkstra ................ | A61N 2/008 |

* cited by examiner

*Primary Examiner* — Ahmed M Farah  
(74) *Attorney, Agent, or Firm* — Vani Moodley, Esq.

(57) ABSTRACT

The present invention relates to a therapeutic pad. The therapeutic pad includes a backlight layer, a light source layer having an avoidance area, and a light emitting layer having a connecting part. The backlight layer includes a receiving portion to receive the light source layer therein. Further, the connecting part is arranged on the light emitting layer at a side facing the receiving portion of the backlight layer. The connecting part passes through the avoidance area of the light source layer to attach the light emitting layer to the backlight layer. The attachment of the light emitting layer with the backlight layer maintains uniform distance between the light emitting layer and the backlight layer, thereby reducing bulging of the light emitting layer during bending to avoid formation of wrinkles on the therapeutic pad.

15 Claims, 11 Drawing Sheets

THERAPEUTIC PAD

TECHNICAL FIELD

The present invention relates to a light therapy. More specifically, the present invention relates to a therapeutic pad used for light therapy.

BACKGROUND

Therapeutic pads are widely used in various medical, therapeutic, and cosmetic applications. The therapeutic pads utilise light-emitting diodes (LEDs) mounted on a lamp board and are configured to deliver specific wavelengths of light through a transparent layer to the user's skin or target area. To ensure effective light delivery and user comfort, the treatment pad structure includes a lamp board which houses and powers the light sources, a backlight layer that reflects light toward the transparent layer, and a transparent layer through which the emitted light exits toward the skin.

A key challenge in treatment pad design arises from the need to maintain firm adhesion between the transparent layer and the underlying layers, especially the backlight layer. This is crucial because treatment pads are frequently subject to bending during application, such as when being applied to curved body surfaces, which generates mechanical stress at the interfaces between layers. Due to the disparity in flexibility and mechanical properties of these layers, especially between the rigid transparent layer and the more flexible backlight layer, conventional assembly methods often fail to provide a robust bond. This results in separation at the interface, which can lead to bulging of the transparent layer. Such deformation can compromise light transmission efficiency, cause user discomfort, and reduce the aesthetic and functional quality of the therapeutic pad.

To address these mechanical challenges, injection moulding is used to affix the transparent layer to the backlight layer and the lamp board. This process involves injecting a molten polymer material into a mold where the components are fixed, allowing for simultaneous bonding and encapsulation of the transparent layer. Injection molding offers better layer integration compared to adhesives or mechanical fasteners, as it can distribute bonding forces uniformly and reduce the risk of localized delamination.

However, the injection molding has significant drawbacks when applied to large-area therapeutic pads. As the surface area increases, the difficulties inherent in injection molding become more pronounced. First, large transparent surfaces are particularly susceptible to foaming during molding, a defect arising from trapped gases or improper thermal control, which manifests as bubbles within the material. These bubbles can distort light transmission and degrade the visual quality of the product. Second, maintaining thickness uniformity in the transparent layer across a wide area is extremely difficult. The flexibility of the backlight layer means that it may deform slightly during the molding process, resulting in uneven support and ultimately causing variations in the thickness of the transparent layer. These thickness variations not only impact optical clarity but may also lead to non-uniform light distribution, diminishing the therapeutic efficacy of the therapeutic pad.

Furthermore, the increased material volume and surface area associated with large therapeutic pads lengthen the cycle time of the injection molding process and elevate the risk of warpage and residual stress, further undermining product quality. These challenges collectively result in a lower production yield, driving up manufacturing costs and affecting commercial scalability.

Therefore, there is a need for a therapeutic pad to overcome a few or all drawbacks of the existing technologies.

STATEMENT OF THE INVENTION

An object of the present invention is to provide a therapeutic pad.

Another object of the present invention is to provide a therapeutic pad that can avoid formation of wrinkles on the light emitting layer.

Yet another object of the present invention is to provide a therapeutic pad that can emit light evenly throughout the entire surface of the therapeutic pad.

Another object of the present invention is to provide a therapeutic pad that hides the internals of the therapeutic pad to provide an aesthetically pleasing and stable therapeutic pad.

One more object of the present invention is to provide a therapeutic pad that maintains firm adhesion between all layers of the therapeutic pad.

According to the present invention, there is provided a therapeutic pad. The therapeutic pad may include a backlight layer, a light emitting layer, and a light source layer arranged between the backlight layer and the light emitting layer.

The backlight layer may have a receiving portion.

The light source layer may be arranged in the receiving portion. The light source layer may include an avoidance area. The light source layer may include a board and a plurality of LED beads arranged on the board to emit the light for phototherapy. The board of the light source layer may comprise a first light strip arranged along a transverse direction of the receiving portion and a plurality of second light strips arranged along the longitudinal direction of the receiving portion. Each end of the second light strip is connected to the first light strip, forming the avoidance area between two adjacent second light strips.

In the present aspect, the avoidance area may be in the form of a long strip. The avoidance area may be configured along the longitudinal direction of the receiving portion on the light source layer. Further, the avoidance area may include a plurality of avoidance zones arranged at intervals along a transverse direction of the receiving portion.

Further, the light emitting layer may be arranged in the receiving portion. The light emitting layer may include a connecting part. The connecting part may be a convex strip. The receiving portion may include a positioning strip to receive the convex strip of the light emitting layer. The positioning strip may include a positioning groove having an open top to receive a top of the convex strip therein. The convex strip may be adhered into the positioning groove using an adhesive material.

The connecting part of the light emitting layer may be passes through the avoidance area of the light source layer to attach the light emitting layer with the receiving portion for maintaining a uniform distance between the light emitting layer and the backlight layer.

In an aspect, the light emitting layer may include a plurality of support rings, positioned corresponding to the plurality of LED beads to prevent the plurality of LED beads from being compressed by the light emitting layer during bending of the therapeutic pad.

In another aspect, the backlight layer may include an installation groove arranged at a bottom of the receiving portion to receive a board of the light source layer therein.

In one more aspect, the light source layer may be hidden by a light shielding layer arranged between the light source layer and the light emitting layer. The light shielding layer may be a flexible board having a plurality of through holes positioned corresponding to the plurality of LED beads of the light source layer.

Further, the light shielding layer may include a slot positioned corresponding to a connecting part of the light emitting layer to allow connection of the connecting part with the receiving portion of the backlight layer.

In an aspect, the backlight layer may include a support frame arranged around the receiving portion of the backlight layer to provide structural support to the therapeutic pad during bending.

In another aspect, the backlight layer may include a circuit board and a battery. The battery is electrically connected to the circuit board, and the circuit board is electrically connected to the light source layer.

The circuit board and the battery may be arranged in the receiving portion of the backlight layer. The backlight layer may be recessed at a bottom of the receiving portion to form an integrated storage unit to receive and store the circuit board and the battery.

In an alternative embodiment, the circuit board and the battery may be arranged in a control box. The control box may be a casing attachable to the backlight layer to connect the circuit board to the light source layer.

BRIEF DESCRIPTION OF DRAWINGS

Other features and advantages of the invention will become apparent when reading the detailed description given below, purely by way of example and in a non-limitative manner, referring to the following figures:

FIG. 6b shows a perspective view of a backlight layer illustrating an embodiment shown in FIG. 6a;

DETAILED DESCRIPTION

An embodiment of this invention, illustrating its features, will now be described in detail. The words "comprising,"

"having," "containing," and "including," and other forms thereof, are intended to be equivalent in meaning and be open-ended in that an item or items following any one of these words is not meant to be an exhaustive listing of such item or items, or meant to be limited to only the listed item or items.

The present invention provides a therapeutic pad. The therapeutic pad is provided to increase the lifecycle of the product by reducing the formation of wrinkles. Further, the therapeutic pad is configured to avoid bulging of the layers during phototherapy, providing a more stable therapeutic pad. The therapeutic pad is configured in such a way that internal components are hidden from a user to provide an aesthetically pleasing device.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

The disclosed embodiments are merely exemplary of the invention, which may be embodied in various forms.

Figure 1:
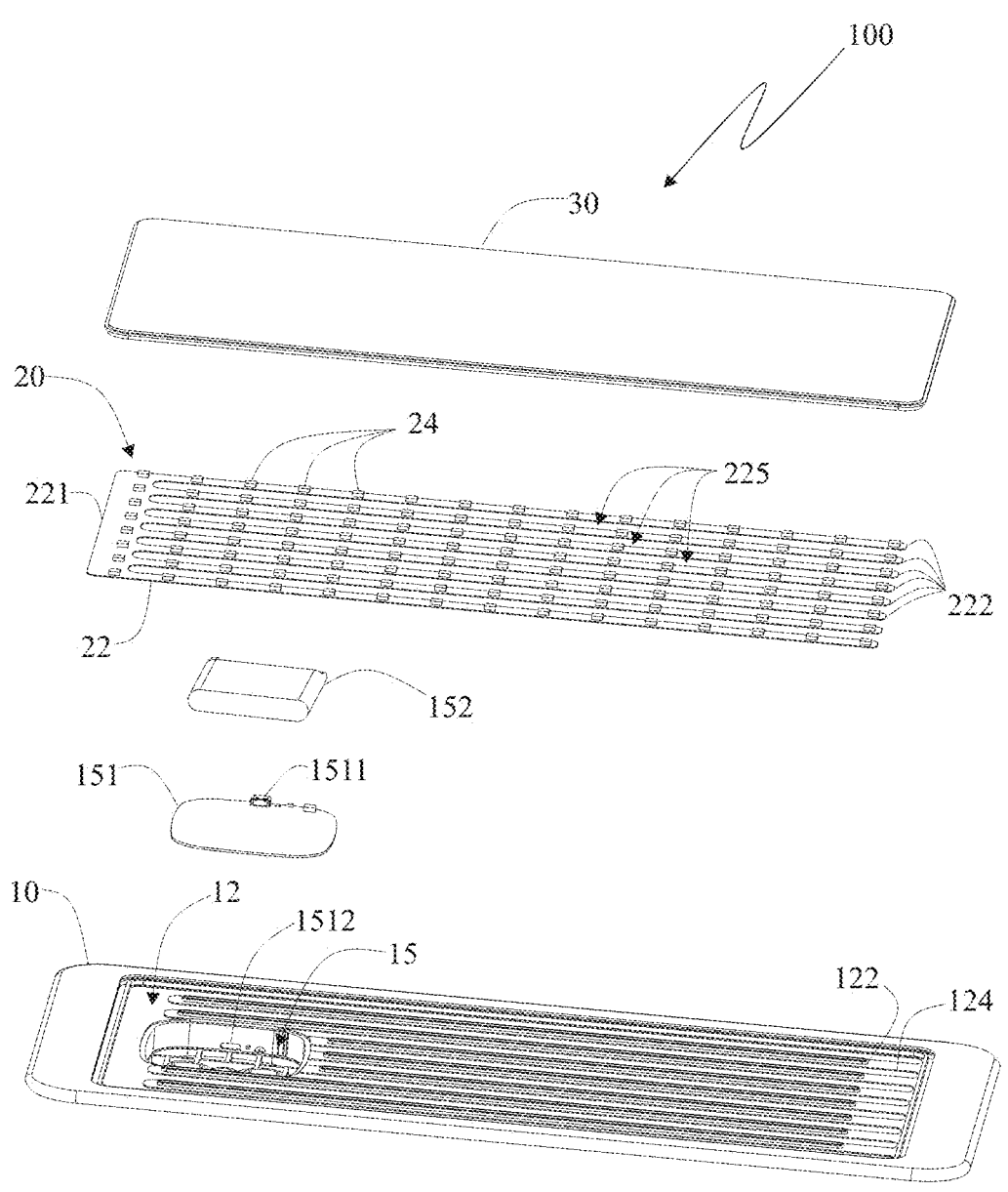
FIG. 1 shows an exploded view of a therapeutic pad in accordance with the present invention.
Figure 2:
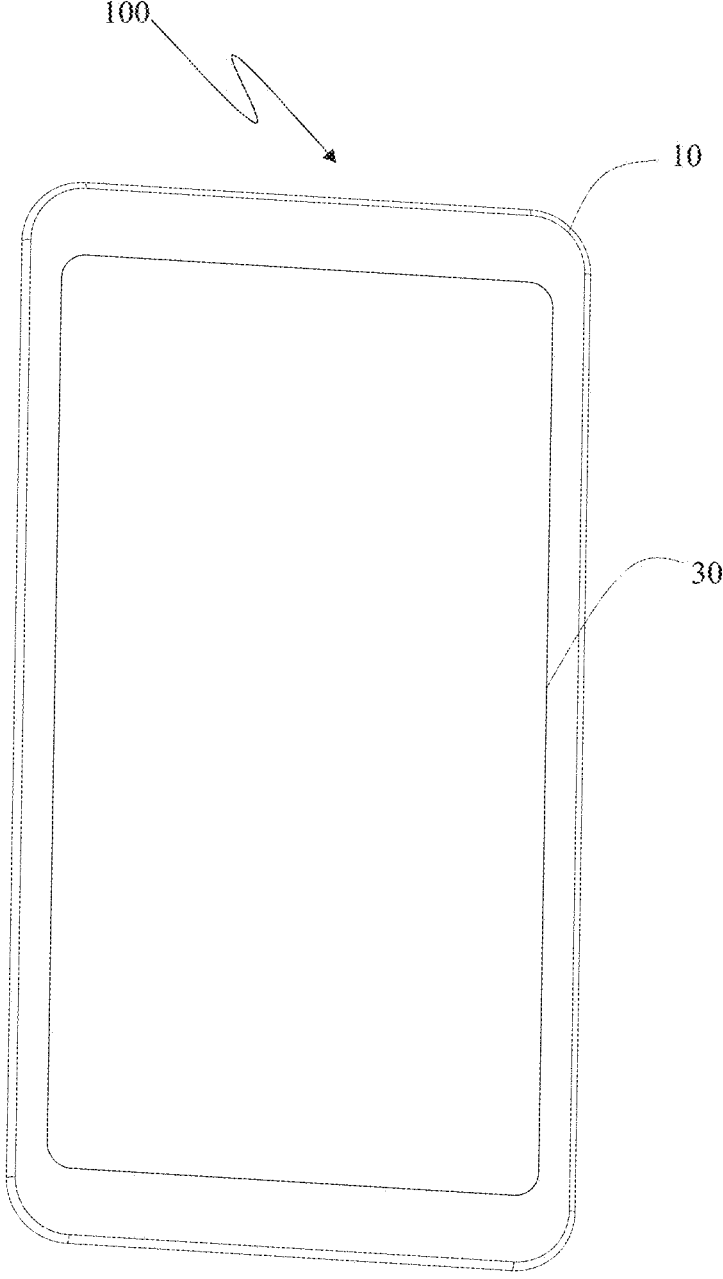
FIG. 2 shows an assembled view of a therapeutic pad in accordance with the embodiment shown in FIG. 1.

Referring now to FIGS. 1, and 2, a therapeutic pad 100 in accordance with the present invention is illustrated. The therapeutic pad 100 includes a backlight layer 10, a light emitting layer 30, and a light source layer 20 arranged between the backlight layer 10 and the light emitting layer 30. The therapeutic pad 100 is used for phototherapy or therapy in areas such as abdomen, back, face, or head. During use, the therapeutic pad 100 is placed against the skin or kept at certain distance from a skin.

The backlight layer 10 is a flexible layer, and one side of the backlight layer 10 is provided with a receiving portion 12. In the present embodiment, the backlight layer 10 is having a rectangular shape. It may be obvious for a person skilled in the art to configure the backlight layer 10 with any other shape, including square, triangular or the like.

Further, the receiving portion 12 is a recessed region of the backlight layer 10, forming a space to accommodate the light source layer 20. The light source layer 20 is provided to emit light for phototherapy. The light source layer 20 includes a board 22 and a plurality of LED beads 24 arranged on the board 22 to emit light for phototherapy. The board 22 has a shape corresponding to a shape of the receiving portion 12 to insert the board 22 therein. In the present embodiment, the receiving portion 12 is having a rectangular shape, hence, the board 22 of the light source layer 20 is having a rectangular shape corresponding to the rectangular shape of the receiving portion 12.

Figure 3:
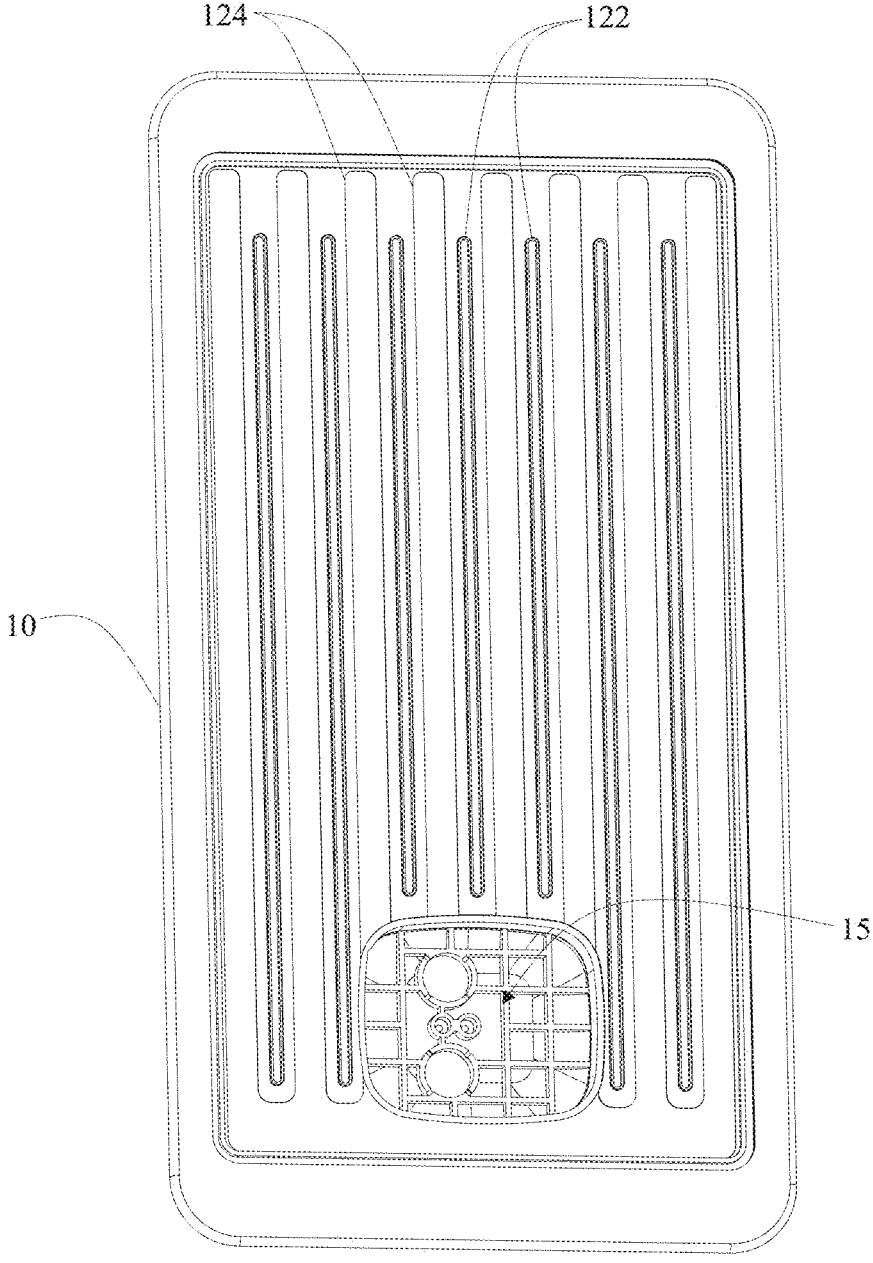
FIG. 3 shows a front view of a backlight layer of the therapeutic pad shown in FIG. 1.
Figure 4:
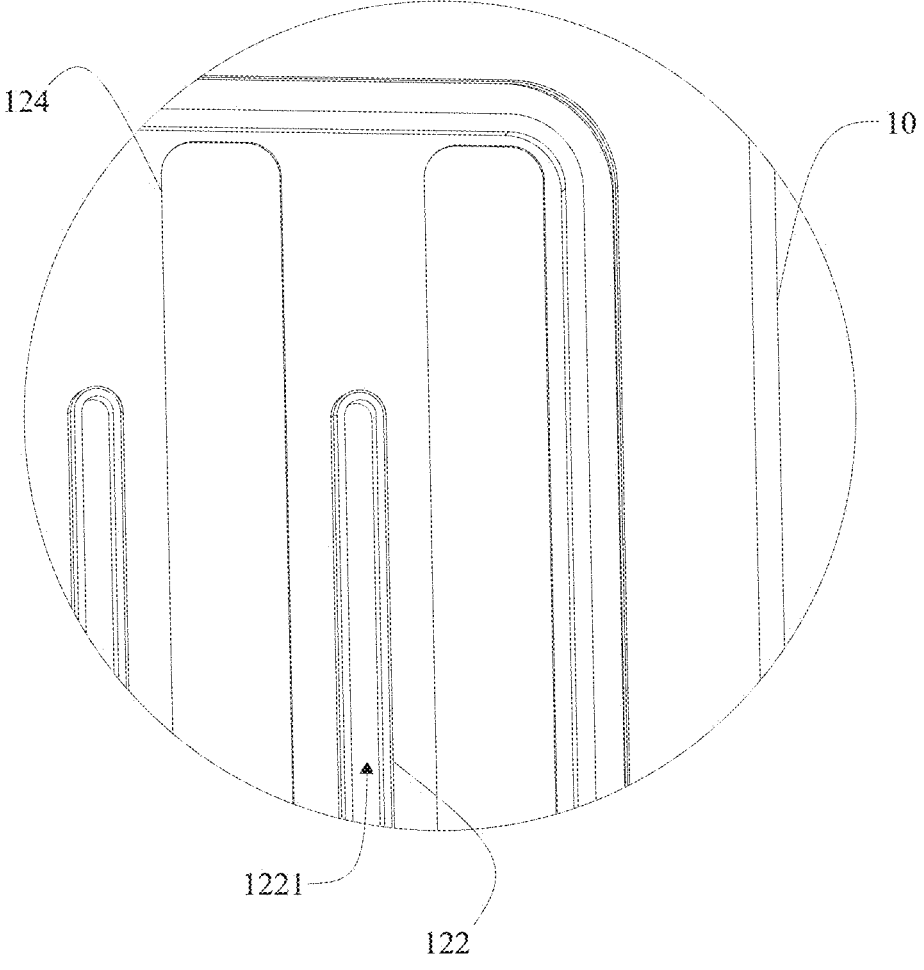
FIG. 4 shows an enlarged view of a portion of the backlight layer shown in FIG. 3.

Referring now to FIGS. 1, 3, and 4, the backlight layer 10 includes an installation groove 124 arranged at a bottom of the receiving portion 12 to receive the board 22 of the light source layer 20 therein.

Specifically, the board 22 of the light source layer 20 comprises a first light strip 221 arranged along a transverse direction of the receiving portion 12 and a plurality of second light strips 222 arranged along a longitudinal direction of the receiving portion 12. Each second strip of the plurality of second light strips 222 has two ends. One end of each second light strip 222 is connected to the first light strip 221, forming an avoidance area 225 between adjacent two second light strips 222. The avoidance area 225 is in a form of a long strip, configured along the longitudinal direction of the receiving portion 12. The avoidance area 225 includes a plurality of avoidance zones arranged at intervals along the transverse direction of the receiving portion 12.

Similarly, the installation groove 124 is configured according to the shape of the board 22, considering the avoidance area 225 as shown in FIG. 3. In the present embodiment, the installation groove 124 has a shape corresponding to a shape of the first light strip 221 and the plurality of second light strips 222. The installation groove 124 allows a positioning of the board 22 to reduce the movement of the board 22 in a plane parallel to a plane of the receiving portion 12 during bending process of the therapeutic pad 100.

Further, the light emitting layer 30 is arranged in the receiving portion 12 of the backlight layer 10 shown in FIG. 2. The light emitting layer 30 is a flexible layer that covers the receiving portion 12. The light emitting layer 30 includes two sides, a first side facing the receiving portion 12 and a second side opposite to the first side, facing away from the receiving portion 12.

Figure 5:
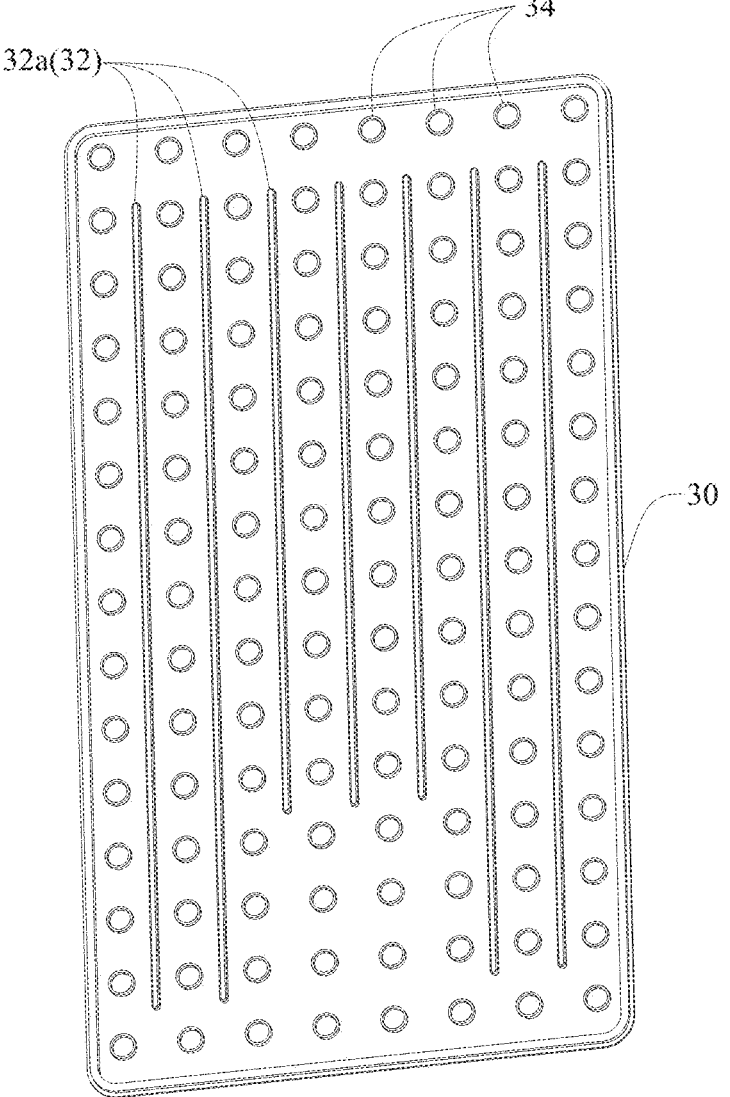
FIG. 5 shows a front view of a light emitting layer of the therapeutic pad shown in FIG. 1.

Referring now to FIGS. 1 and 5, the light emitting layer 30 is a transparent or semi-transparent silicone layer adapted to allow transmission of the light from the light source layer 20 to the skin during phototherapy. The light emitting layer 30 of the therapeutic pad 100 is placed against the skin or kept at a certain distance from the skin during use of the therapeutic pad 100. Especially, the second side of the light emitting layer 30 is placed against the skin for phototherapy.

The light emitting layer 30 includes a connecting frame arranged around a periphery of the light emitting layer 30. The connecting frame is fixedly attached to the first side of the receiving portion 12. The connecting frame facilitates connection of the light emitting layer 30 with the backlight layer 10 to cover the receiving portion 12.

Further, the light emitting layer 30 includes a connecting part 32, especially, the first side of the light emitting layer 30 includes the connecting part 32. The connecting part 32 is configured to pass through the avoidance area 225 as shown in FIG. 1 of the light source layer 20 and is connected to the bottom of the receiving portion 12.

In the present embodiment, the connecting part 32 of the light emitting layer 30 is a convex strip 32a passing through the avoidance area 225 of the light source layer 20 to attach the light emitting layer 30 to the receiving portion 12. The convex strip 32a is adhered to the bottom of the receiving portion 12 of the backlight layer 10 using an adhesive material. The adhesive material can be silicone adhesives, acrylic adhesives, epoxy adhesives, polyurethane adhesives, hot melt adhesives, pressure-sensitive adhesives PSA, UV-curable adhesives, cyanoacrylate adhesives, anaerobic adhesives, and thermosetting adhesives. In alternative embodiments, the connecting part 32 can be a connecting column, convex rib, or grid structure.

Referring again to FIGS. 3, 4, and 5, the receiving portion 12 includes a positioning strip 122 to receive the convex strip 32a of the light emitting layer 30. The positioning strip 122 includes a positioning groove 1221 having an open top to receive a top of the convex strip 32a therein. The convex strip 32a has a curved top adapted to insert into the positioning groove 1221. The curved top provides ease in inserting the connecting part 32 into the positioning groove 1221. The convex strip 32a is attached and pasted into the positioning groove 1221 to secure the connection between the light emitting layer 30 and the backlight layer 10. The positioning groove 1221 is configured to receive the convex strip 32a to hide adhesive bonding traces. The convex strip 32a as the connecting part 32 inserted within the position groove 1221 and adhered using the adhesive material provides firm adhesion between the light emitting layer 30 and the backlight layer 10.

The connecting part 32 is configured along the longitudinal direction of the receiving portion 12 corresponding to the avoidance area 225 of the light source layer 20. In the preferred embodiment, the connecting part 32 includes a plurality of convex strips 32a configured on the first surface of the light emitting layer 30. The number of the plurality of convex strips 32a is based on the area of the light emitting layer 30 or the receiving portion 12 of the backlight layer 10.

The plurality of convex strips 32a is configured according to the position of the plurality of avoidance zones of the avoidance area 225. Similarly, the backlight layer 10 includes a plurality of positioning strips 122 arranged in the receiving portion 12 to receive the plurality of convex strips 32a passing through the plurality of avoidance zones. The plurality of avoidance zones facilitates the positioning of the positioning strip 122 and the convex strip 32a of the connecting part 32 passing through the light source layer 20.

The convex strip 32a is configured to attach a portion of the light emitting layer 30 to the backlight layer 10. The plurality of convex strips 32a is connected to the corresponding positioning strip 122 of the plurality of positioning strips 122 for maintaining uniform distance between the light emitting layer 30 and the backlight layer 10 during bending of the therapeutic pad 100. The uniform distance between the light emitting layer 30 and the backlight layer 10 is maintained to reduce wrinkles caused by bending of the therapeutic pad 100.

The backlight layer 10 and the light emitting layer 30 are flexible layers to enable the therapeutic pad 100 to bend and adapt to the user's body surface. The connecting part 32 arranged on the light emitting layer 30 and connecting it to the bottom of the receiving portion 12, facilitates prevention of local bulging and wrinkling of the light emitting layer 30 during the bending process of the therapeutic pad 100, and provides a curved and smoother surface to the light emitting layer 30 when the therapeutic pad 100 is bent.

Referring again to FIG. 5, the light emitting layer 30 includes a plurality of support rings 34, positioned corresponding to the plurality of LED beads 24 of the light source layer 20 shown in FIG. 1. Each support ring of the plurality of support rings 34 is arranged around the corresponding LED beads 24 to prevent the plurality of LED beads 24 from being compressed by the light emitting layer 30 during bending of the therapeutic pad 100.

Figure 6A:
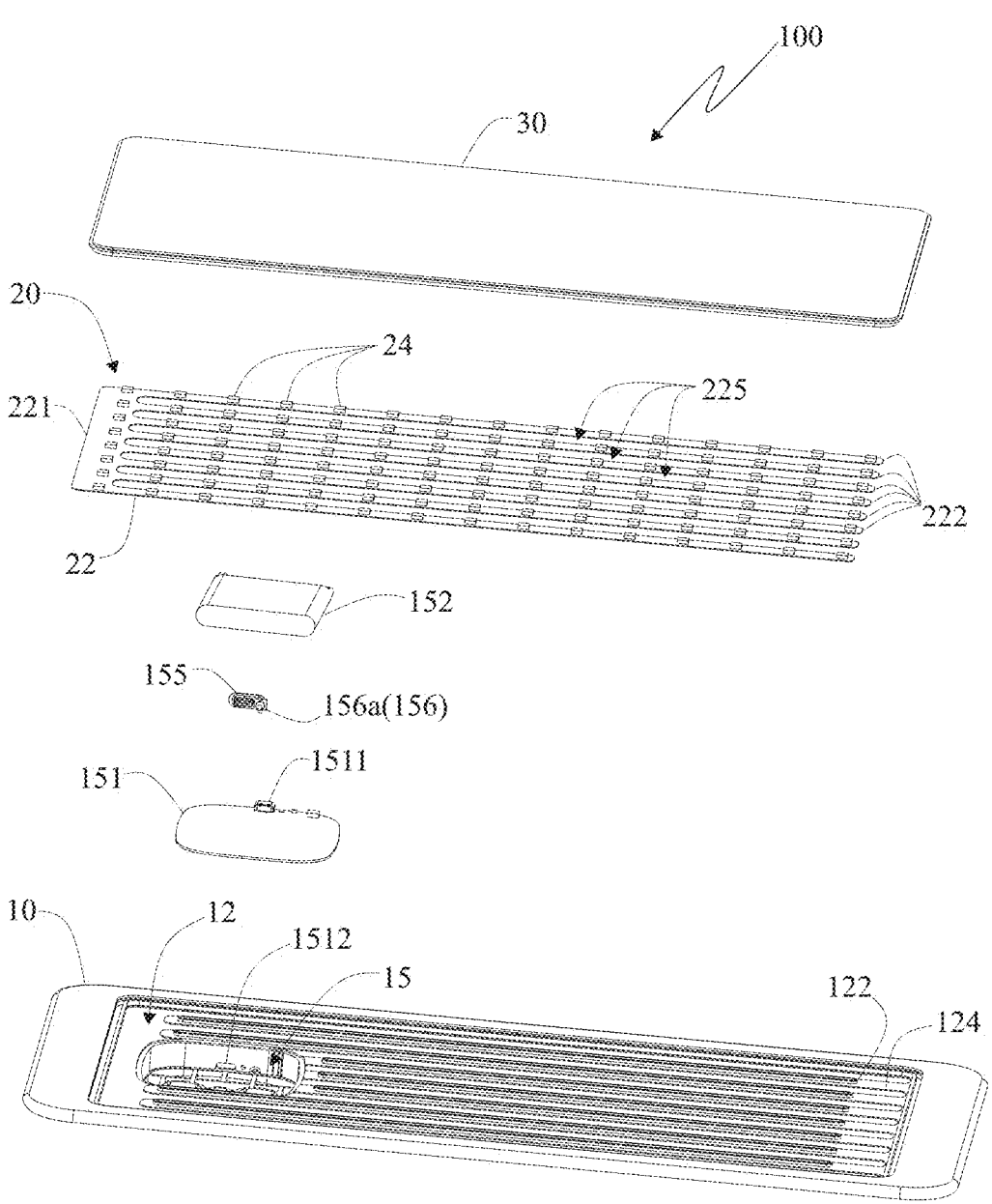
FIG. 6a shows an exploded view of a therapeutic pad in accordance with another embodiment of the present invention.
Figure 6B:
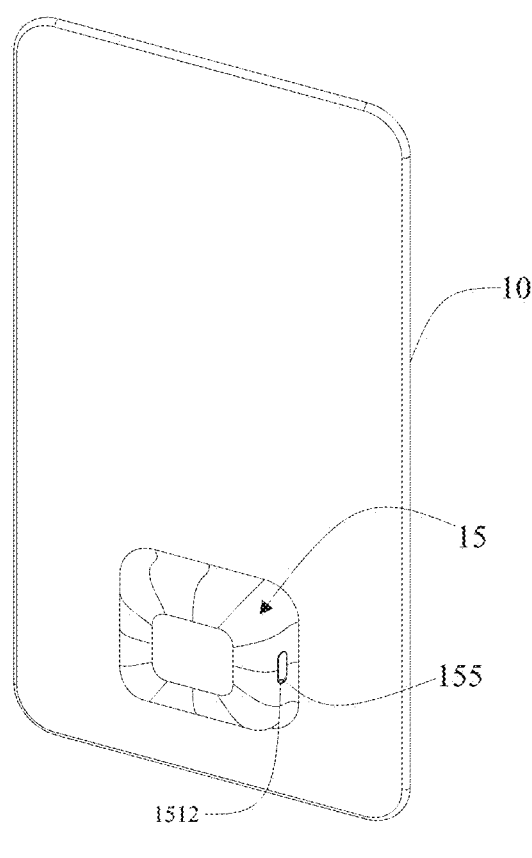

Referring now to FIGS. 6a and 6b, the backlight layer 10 includes a circuit board 151, and a battery 152. The battery 152 is electrically connected to the circuit board 151, and the circuit board 151 is electrically connected to the light source layer 20. The circuit board 151 and the battery 152 are arranged in the receiving portion 12 of the backlight layer 10. Specifically, the backlight layer 10 is recessed at the bottom of the receiving portion 12 to form an integrated storage unit 15 to receive and store the circuit board 151 and the battery 152. The integrated storage unit 15 is a hollow space to accommodate the circuit board 151 and the battery 152. The battery 152 and the circuit board 151 are integrated onto the therapeutic pad 100 for user convenience.

The circuit board 151 is arranged on the side of the battery 152 away from the light emitting layer 30. In an embodiment, a foam pad not shown is provided between the circuit board 151 and the battery 152 to provide cushioning and help protect the battery 152.

In an embodiment, a cover plate not shown is provided on the side of the battery 152 near the light emitting layer 30. The cover plate is in contact with the backlight layer 10. The cover plate can be a plastic or a hard board to maintain the stability of the battery 152.

Further, the circuit board 151 includes a charging port 1511. Additionally, the backlight layer 10 includes a charging hole 1512 arranged at a position corresponding to the charging port 1511 to provide an opening to the charging port 1511.

Furthermore, the backlight layer 10 includes a cover 155 to cover the charging hole 1512 of the backlight layer 10, and a connector 156 to connect the cover 155 to the backlight layer 10 to facilitate opening and closing of the cover 155 to access the charging port 1511 through the charging hole 1512. The connector 156 is a rotating shaft 156a inserted into the backlight layer 10. The rotating shaft 156a facilitates a rotational movement of the cover 155 upon applying an external force on the cover 155, thereby opening or closing the charging hole 1512.

Figure 7:
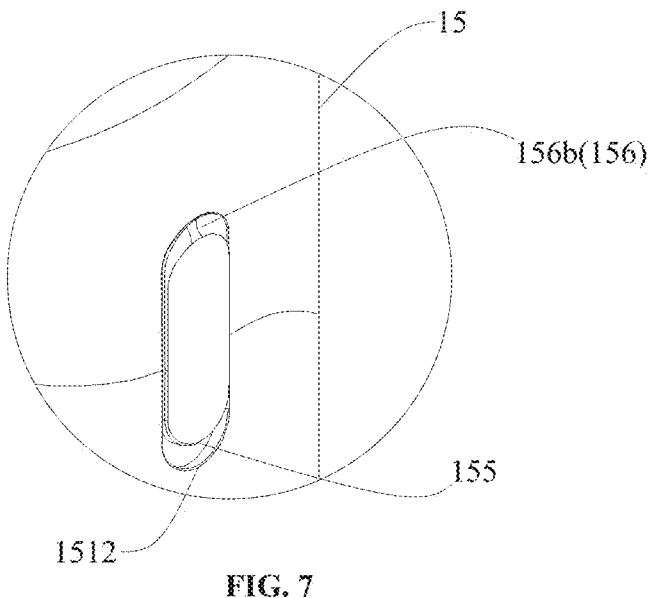
FIG. 7 shows a perspective view of a cover of the therapeutic pad shown in accordance with an alternative embodiment of the present invention.

In an alternative embodiment, as shown in FIG. 7, the connector 156 is a flexible element 156b connecting the backlight layer 10 and the cover 155. The flexible element 156b allows the movement of the cover 155 upon applying an external force for opening and closing the charging hole 1512. The cover 155 prevents dust and foreign objects from entering the therapeutic pad 100 through the charging hole 1512.

Figure 8:
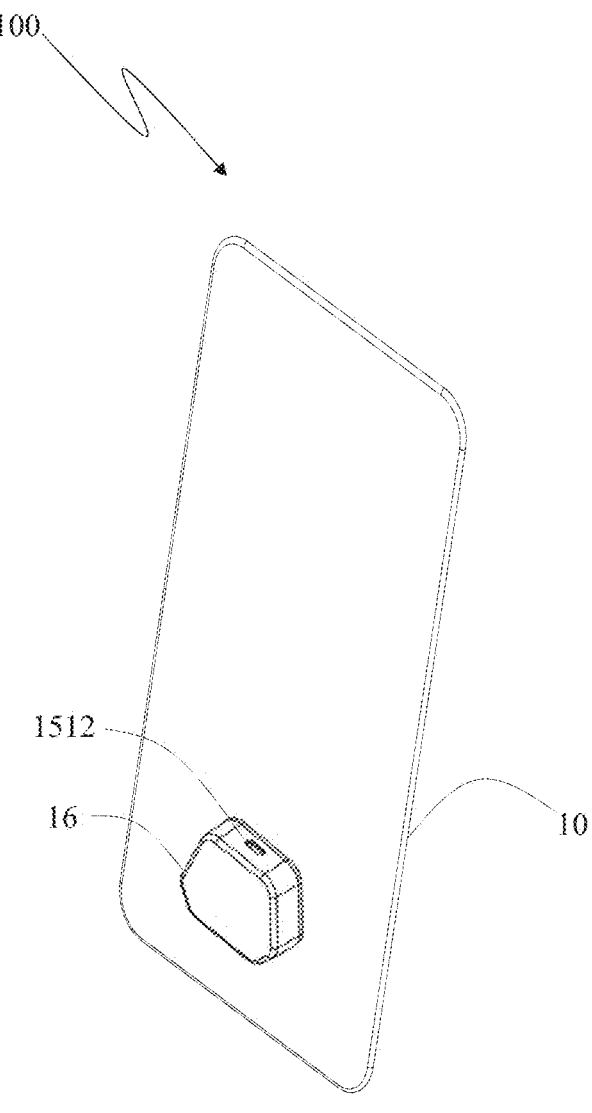
FIG. 8 shows a rear perspective view of the therapeutic pad in accordance with one more embodiment of the present invention.

In another embodiment, as shown in FIG. 8, the circuit board 151 and the battery 152 are arranged in a control box 16. The control box 16 is a casing attachable to the backlight layer 10 of the therapeutic pad 100 to connect the circuit board 151 to the light source layer 20. The control box 16 is a hard plastic or metal box which can be embedded within the backlight layer 10 or detachably connected to the backlight layer 10 through magnetic electrodes.

Figure 9:
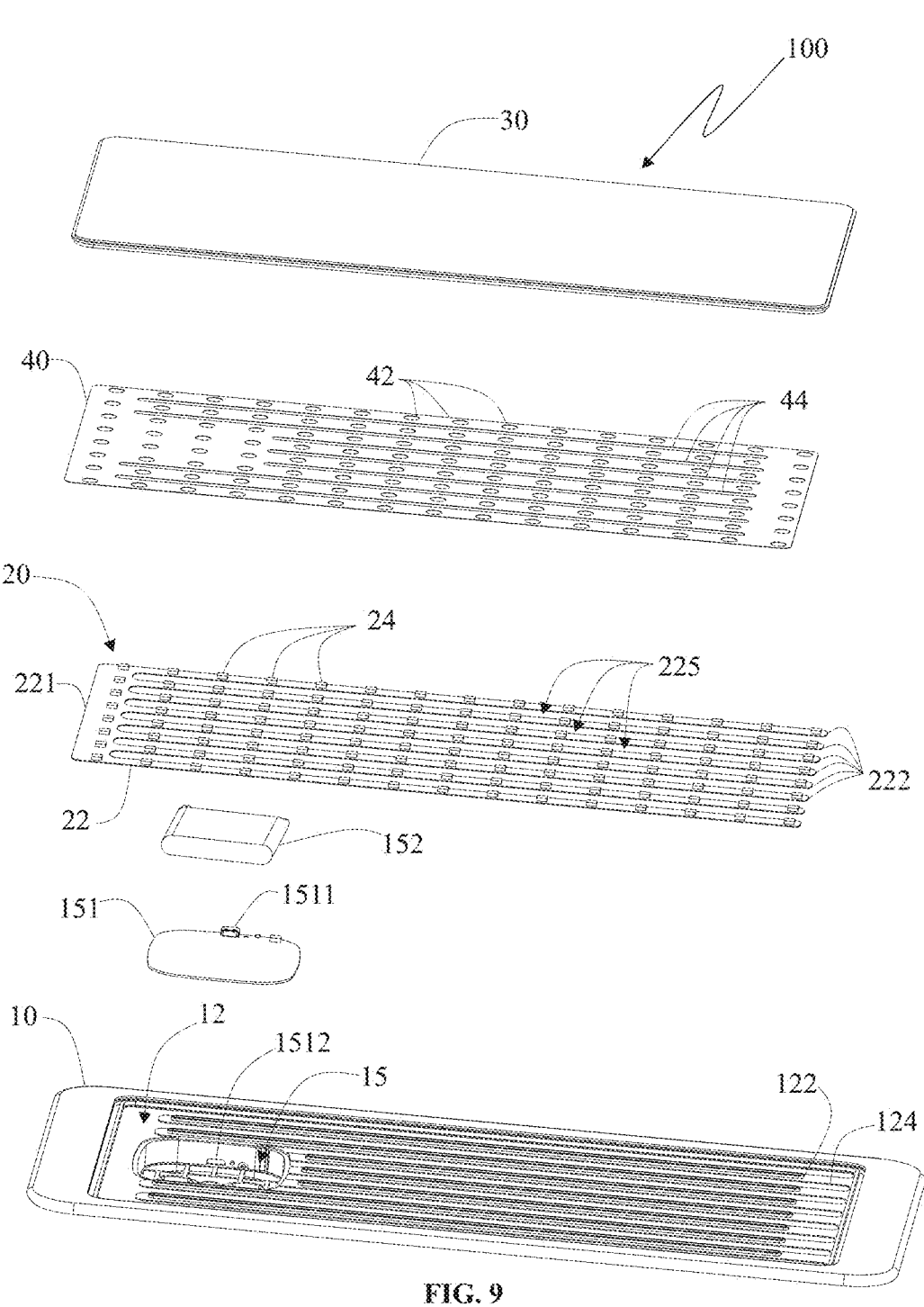
FIG. 9 shows an exploded view of a therapeutic pad in accordance with an embodiment having a light shielding layer.

In an embodiment shown in FIG. 9, the therapeutic pad 100 includes a light shielding layer 40. The light source layer 20 is hidden by the light shielding layer 40. The light shielding layer 40 is arranged between the light source layer 20 and the light emitting layer 30 to restrict the user from seeing the light source layer 20 directly through the light emitting layer 30. The light shielding layer 40 is provided to hide the adhesive bonding traces for better aesthetics.

The light shielding layer 40 is a flexible board having a plurality of through holes 42 positioned corresponding to the plurality of LED beads 24 of the light source layer 20. Further, the light shielding layer 40 includes a slot 44 positioned corresponding to the connecting part 32 of the light emitting layer 30 to allow connection of the connecting part 32 with the receiving portion 12 of the backlight layer 10. The plurality of through holes 42 for the plurality of LED beads 24 allows the plurality of LED beads 24 to emit light towards the light emitting layer 30. The slot 44 for the connecting part 32 allows connection of the connecting part 32 and the positioning strip 122. Further, the plurality of through holes 42 reduces light leakage from the backlight layer 10 and improves a light utilization efficiency. The positioning groove 1221 is configured to receive the convex strip 32a to hide adhesive bonding traces.

In an embodiment, the light emitting layer 30 is a transparent or semitransparent silicone layer.

In alternative embodiments, the backlight layer 10 is a silicone layer or rubber layer or the backlight layer 10 is a silicone plate formed by injection molding. The light emitting layer 30 and the backlight layer 10 are both flexible layers having a certain degree of elasticity and the ability to bend.

In an embodiment, the light emitting layer 30 is a transparent silicone layer or TPU layer. In an alternative embodiment, the light emitting layer 30 can be a silicone plate formed by injection molding. The light emitting layer 30 and the backlight layer 10 are first processed separately and then assembled.

Further, the connecting part 32 can be injection molded as a whole with the light emitting layer 30, which facilitates processing of the light emitting layer 30 and the connecting part 32 together.

Figure 10:
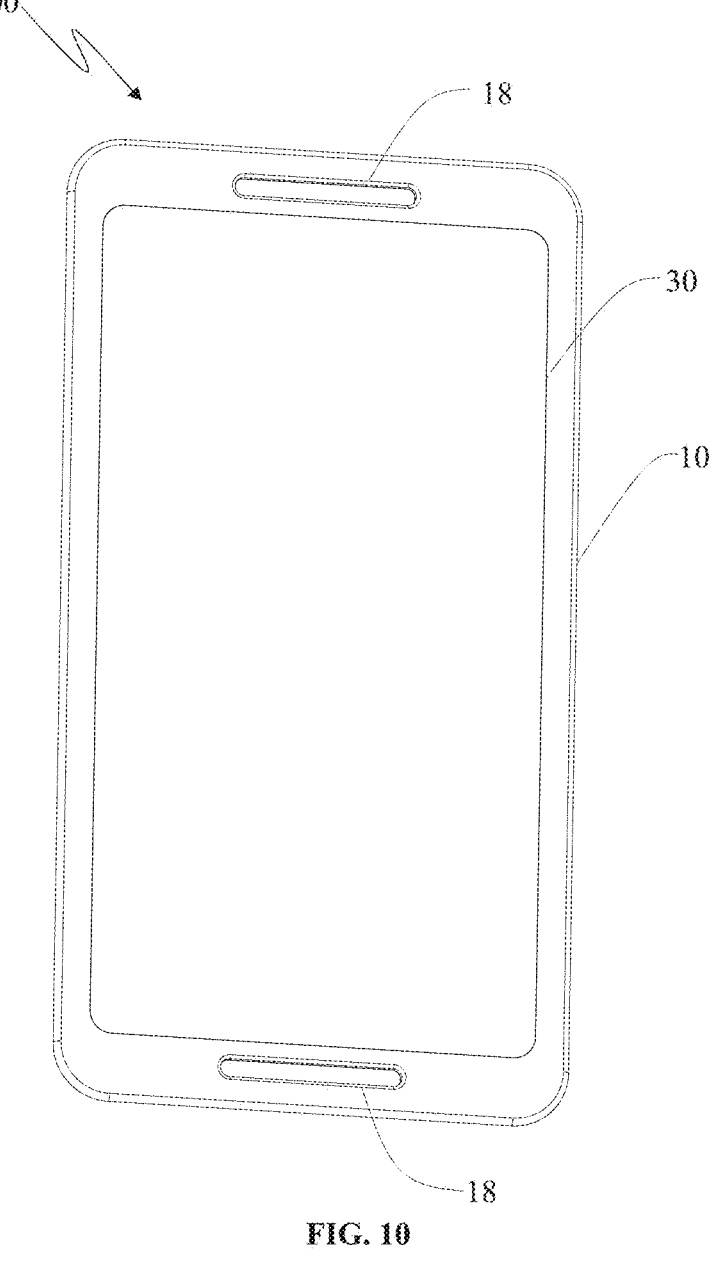
FIG. 10 shows a front view of a therapeutic pad in accordance with one of the embodiments of the present invention.

In an embodiment shown in FIG. 10, the backlight layer 10 is provided with attachment holes 18. The two attachment holes are provided at longitudinal ends of the backlight layer 10 for strap connection. In an alternative embodiment, the backlight layer 10 may include two attachment holes arranged at transversal ends of the backlight layer 10 for strap connection.

Figure 11:
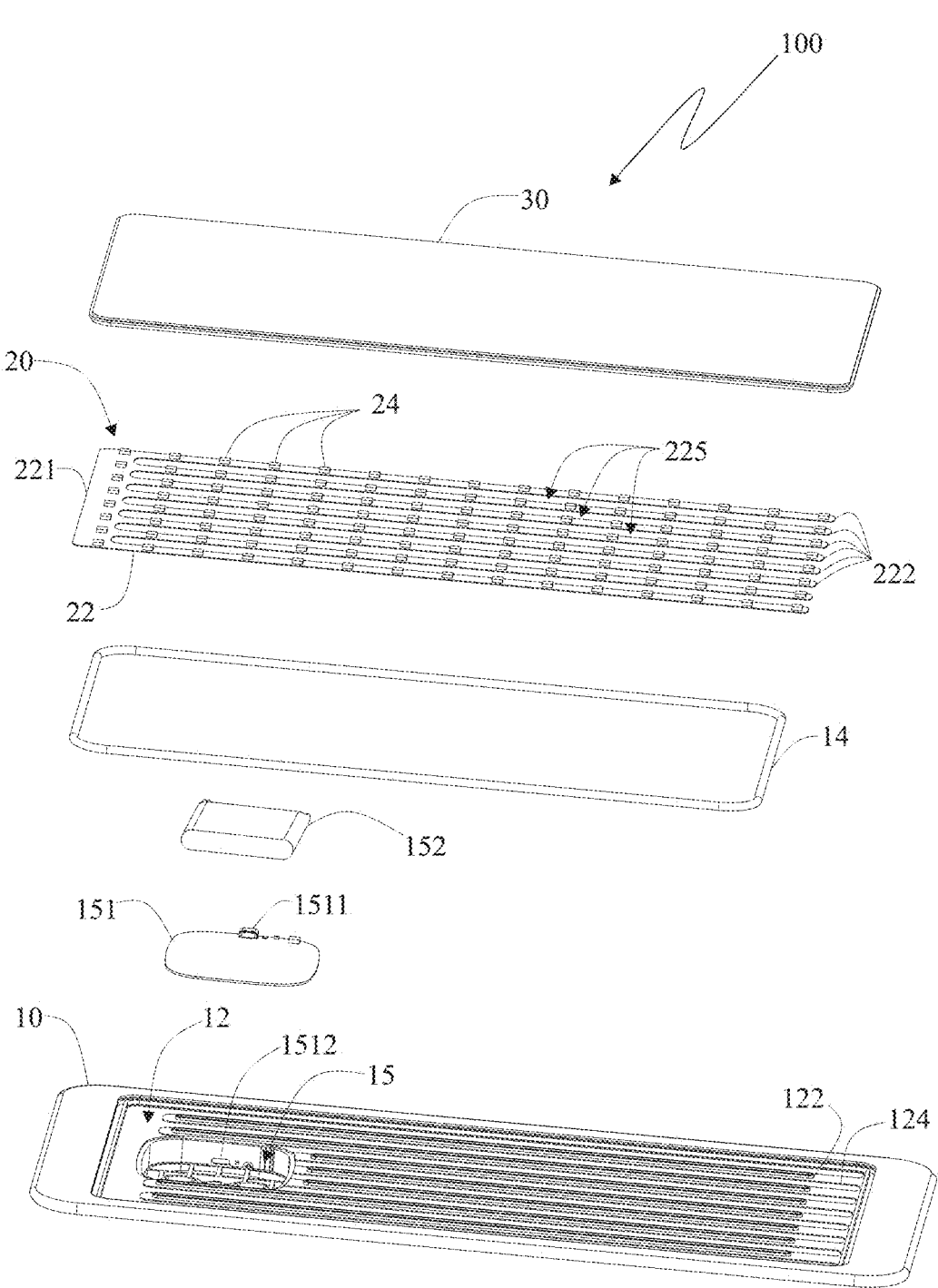
FIG. 11 shows an exploded view of a therapeutic pad in accordance with one of the embodiments of the present invention.

Referring now to FIG. 11, in an embodiment, the backlight layer 10 includes a support frame 14 arranged around the receiving portion 12 of the backlight layer 10. The support frame 14 is having rectangular shape similar to the receiving portion 12. The support frame 14 is provided to maintain stability of the therapeutic pad 100 shape during the bending process of the therapeutic pad 100. In the preferred embodiment, the support frame 14 is a metal frame, such as a steel frame or an aluminium frame, to maintain a curvature when bending during phototherapy process, and to flatten the therapeutic pad 100 again after phototherapy. It may be obvious for a person skilled in the art to configure the support frame 14 with any other material that can maintain curvature during phototherapy and flatten the therapeutic pad 100 again after the phototherapy.

Therefore, the present invention has the advantage of providing a therapeutic pad which avoids the formation of wrinkles on the light emitting layer. Further, the light emitting layer is connected to the backlight layer in such a way that the light source layer can emit the light evenly throughout entire surface of the light emitting layer. The light shielding layer arranged between the light emitting layer and the light source layer hides the internals of the therapeutic pad, especially the adhesive marks are hidden to provide an aesthetically pleasing and stable therapeutic pad.

The foregoing descriptions of specific embodiments of the present invention have been presented for purposes of illustration and description. They are not intended to be exhaustive or to limit the present invention to the precise forms disclosed, and obviously, many modifications and variations are possible in light of the above teaching. The embodiments were chosen and described in order to explain the principles of the present invention best and its practical application, thereby enabling others skilled in the art to best utilize the present invention and various embodiments with various modifications as are suited to the particular use contemplated. It is understood that various omission and substitutions of equivalents are contemplated as circumstance may suggest or render expedient, but such are intended to cover the application or implementation without departing from the scope of the claims of the present invention.

The invention claimed is:

1. A therapeutic pad comprising:
a backlight layer having a receiving portion;
a light source layer arranged in the receiving portion, wherein the light source layer includes an avoidance area; and
a light emitting layer arranged in the receiving portion, the light emitting layer includes a connecting part;
wherein, the connecting part of the light emitting layer passes through the avoidance area of the light source layer to attach the light emitting layer with the receiving portion for maintaining a uniform distance between the light emitting layer and the backlight layer, and wherein the backlight layer includes a circuit board and a battery, the battery being electrically coupled to the circuit board, and the circuit board being electrically coupled to the light source layer.

2. The therapeutic pad as claimed in claim 1, wherein the connecting part is a convex strip, and the receiving portion includes a positioning strip to receive the convex strip of the light emitting layer.

3. The therapeutic pad as claimed in claim 2, wherein the positioning strip includes a positioning groove having an open top to receive a top of the convex strip therein, wherein the convex strip is adhered into the positioning groove using an adhesive material.

4. The therapeutic pad as claimed in claim 1, wherein the light source layer includes a board and a plurality of LED beads arranged on the board to emit the light for photo-therapy.

5. The therapeutic pad as claimed in claim 4, wherein the board of the light source layer comprises a first light strip arranged along a transverse direction of the receiving portion and a plurality of second light strips arranged along a longitudinal direction of the receiving portion, with each end of the second light strip are connected to the first light strip, forming the avoidance area between two adjacent second light strips.

6. The therapeutic pad as claimed in claim 5, wherein the avoidance area is in the form of a long strip, configured along the longitudinal direction of the receiving portion on the light source layer.

7. The therapeutic pad as claimed in claim 6, wherein the avoidance area includes a plurality of avoidance zones arranged at intervals along a transverse direction of the receiving portion.

8. The therapeutic pad as claimed in claim 1, wherein the light emitting layer includes a plurality of support rings, positioned corresponding to a plurality of LED beads to prevent the plurality of LED beads from being compressed by the light emitting layer during bending of the therapeutic pad.

9. The therapeutic pad as claimed in claim 1, wherein the backlight layer includes an installation groove arranged at a bottom of the receiving portion to receive a board of the light source layer therein.

10. The therapeutic pad as claimed in claim 1, wherein the light source layer is hidden by a light shielding layer arranged between the light source layer and the light emitting layer.

11. The therapeutic pad as claimed in claim 10, wherein the light shielding layer is a flexible board having a plurality of through holes positioned corresponding to a plurality of LED beads of the light source layer.

12. The therapeutic pad as claimed in claim 10, wherein the light shielding layer includes a slot positioned corresponding to a connecting part of the light emitting layer to allow connection of the connecting part with a receiving portion of a backlight layer.

13. The therapeutic pad as claimed in claim 1, wherein the backlight layer includes a support frame arranged around the receiving portion of the backlight layer to provide structural support to the therapeutic pad during bending.

14. The therapeutic pad as claimed in claim 1, wherein the circuit board and the battery are arranged in a receiving portion of the backlight layer, wherein the backlight layer is recessed at a bottom of the receiving portion to form an integrated storage unit to receive and store the circuit board and the battery.

15. The therapeutic pad as claimed in claim 1, wherein the circuit board and the battery are arranged in a control box, the control box is a casing attachable to the backlight layer to connect the circuit board to the light source layer.

* * * * *